United States Patent
Yellen (12)

(10) Patent No.: US 6,291,442 B1
(45) Date of Patent: Sep. 18, 2001

(54) PHARMACOLOGICAL MODULATORS OF VOLTAGE-GATED POTASSIUM ION CHANNELS

(75) Inventor: Gary I. Yellen, Newton Highlands, MA (US)

(73) Assignee: The General Hospital Corporation, Boston, MA (US)

(*) Notice: Subject to any disclaimer, the term of this patent is extended or adjusted under 35 U.S.C. 154(b) by 0 days.

(21) Appl. No.: 09/243,675

(22) Filed: Feb. 2, 1999

Related U.S. Application Data (60) Provisional application No. 60/073,482, filed on Feb. 3, 1998.

(51) Int. Cl.$^7$ ............................ A61K 31/63; A61K 31/04

(52) U.S. Cl. ............................................ 514/155; 514/610

(58) Field of Search ........................................ 514/155, 610

(56) References Cited

U.S. PATENT DOCUMENTS

| | | | |
|---|---|---|---|
| 3,789,073 | * 1/1974 | Narayanan et al. | 260/558 A |
| 5,373,009 | 12/1994 | Commons et al. | 514/228.2 |
| 5,401,769 | 3/1995 | Commons et al. | 514/468 |
| 5,464,746 | 11/1995 | Fino | 435/6 |
| 5,545,760 | 8/1996 | Walters et al. | 568/321 |

FOREIGN PATENT DOCUMENTS

| | | |
|---|---|---|
| 195 01 303 A1 | 7/1996 | (DE). |
| 0 755 934 A1 | 1/1997 | (EP). |
| 6-293883 | 10/1994 | (JP). |
| 7-53950 | 2/1995 | (JP). |
| WO 93/24442 A1 | 12/1993 | (WO). |
| WO 94/12621 | 6/1994 | (WO). |
| WO 9619458 | 6/1996 | (WO). |

OTHER PUBLICATIONS

Kishore, V., et al., "Synthesis of α–Poly–[N$^ε$–(2–aryl$^{Δ2}$–thiazoline–4–carbonyl)–L–lysines] with Antiviral Activity," *Indian Journal of Chemistry* 15B:255–257 (1977).

Cramer, R. and Coulson, D.R., "Nickel–Catalyzed Displacement Reactions of Aryl Halides," *J. of Org. Chem.* 40(16):2267–2273 (1975).

Dhareshwar, G.P. and Hosangadi, B.D., "Novel Rearrangement of 2–Thiophenoxybenzhydroxamic Acid to 2–Carboxamidodiphenyl Sulphoxide," *Indian Journal of Chemistry* 16B:143–144 (1978).

Brown, P.M., et al., "Persulphate Oxidations. Part V. Oxidation of 0–(Arylthio)– and 0–(Arylsulphonyl)–benzoic Acids," *J. Chem. Soc. Perkin Trans. I*:2842–2846 (1972).

Brannigan, L.H., et al., "Biologically Oriented Organic Sulfur Chemistry. 14. Antiinflammatory Properties of Some Aryl Sulfides, Sulfoxides, and Sulfones," *J. of Med. Chem.* 19(6):798–802 (1976).

Schwarz, T.L., et al., "Multiple potassium–channel components are produced by alternative splicing at the Shaker locus in Drosophila," *Nature* 331:137–142 (1988).

Timpe, L.C., et al., "Expression of functional potassium channels from Shaker cDNA in *Xenopus oocytes,*" *Nature* 331:143–145 (1988).

Holmgren, M., et al., "On the Use of Thiol–modifying Agents to Determine Channel Topology," *Neuropharmacology* 35(7):797–804 (1996).

Holmgren, M., et al., "N–type Inactivation and the S4–S5 Region of the Shaker K$^+$ Channel," *J. Gen. Physiol.* 108:195–206 (1996).

Liu, Y., et al., "Dynamic Rearrangement of the Outer Mouth of a K$^+$ Channel during Gating," *Neuron* 16:859–867 (1996).

Liu, Y., et al., "Gated Access to the Pore of a Voltage–Dependent K$^+$ Channel," *Neuron* 19:175–184 (1997).

Jurman, M.E., et al., "Visual Identification of Individual Transfected Cells for Electrophysiology Using Antibody–Coated Beads," *BioTechniques* 17(5):876–881 (1994).

Armstutz, E.D. and Neumoyer, C.R., "Studies in the Sulfone Series. III. The Preparation and Properties of 2, 8–Diaminothiaxabthone– and 2,8–Thiaxanthene–5–dioxides and Some Related Compounds," *J. Am. Chem. Soc.* 69:1925–1929 (1947).

Jagroop, C.L. and Charlestown, E.H., "The Bromination of 1–Nitro–, 1–Bromo–, and 1–Acetamidofluoranthene," *Proc. R.S.E. (A)* 71(3):193–197 (1973).

Kazankov, M.V. and Ginodman, L.G., "Replacement of an AZO Group on Reaction with Amines," Sci.–Res. Inst. of Org. Intermediates and Dyes, Moscow, trans. from *Zhurnal Organicheskoi Khimii* 11(2):46–457 (1975).

Noyce, D.S. and Kittle, P.A., "The Effect of Substituents on the Rate of Formation of Substituted Anthraquinones," *J. Org. Chem.* 32:2459–2462 (1967).

Chandy, K.G. and Gutman, G.A., "Voltage–gated K+ Channel Genes," in *Handbook of Receptors and Channels: Ligand– and Voltage–gated Ion Channels*, R.A. North, ed. (Boca Raton: CRC Press), pp. 1–71 (1995).

(List continued on next page.)

*Primary Examiner*—Kevin E. Weddington
(74) *Attorney, Agent, or Firm*—Hamilton, Brook, Smith & Reynolds, P.C.

(57) ABSTRACT

Disclosed herein is the discovery that an allosteric receptor site exists on the intracellular surface of Shaker class voltage-gated potassium ion channels that is distinct from the pore and is involved in regulating gating of the pore. A class of compounds has been identified that binds to this allosteric site and modulates the length of time the channel remains open. Based on these discoveries, novel methods of modulating the activity of Shaker class voltage-gated potassium ion channels and assays for determining which compounds are modulators of these ion channels are reported herein.

23 Claims, 4 Drawing Sheets

OTHER PUBLICATIONS

Mann, F.G. and Turnbull, J.H., "Xanthones and Thioxanthones. Part I. The Synthesis of 2– and 3–Dialkylaminoalkylamino–derivatives," *J. Chem. Soc.*:747–756 (1951).

Goldberg, A.A. and Walker, H.A., "Synthesis of Diaminoxanthones," *J. Chem. Soc.*:1348–1357 (1953).

Campbell, N. and Wilshire, J.F.K., "The Preparation of 2–Substituted Fluoranthenes," *J. Chem. Soc.*:867–869 (1954).

Kliegl, *Chem. Ber. 38*:294–295 (1905).

Rainer, J., *Monatsh. Chem.*, 29:178–179 (1908).

Chardonnens, L. and Heinrich, P., "Sur l'aptitude réactionnelle du groupement méthylique VIII. Formation d'anilides par l'action des nitroso–dérivés sur des composés à groupement méthylique actif," *Helv. Chim. Acta*, 27:321–331 (1944).

Mayer, F., "Derivate der Thiosalicylsäure und der Thioxanthons," *Chem. Ber. 42*:3046–3049; 3066–3067 (1909).

Busch, A.E. and Suessbrich, H., "Participation of the $I_{sK}$ protein in regulation and pharmacological properties oof the $I_{minK}$ channel complex," *European Journal of Physiology 434*(5):R95–96 (1997).

Livant, P. and Martin, J.C., "Polarizability of the Hypervalent Bond in Some Unsymmetrically Substituted Sulfuranes as Reflected in Carbonyl Stretching Frequencies of Acyloxy Ligands," *J. Am. Chem. Soc. 99*(17):5761–5767 (1977).

Hamill, O.P., et al., "Improved Patch–Clamp Techniques for High–Resolution Current Recording from Cells and Cell–Free Membrane Patches," *Pfluegers Arch 391*:85–100 (1981).

Shieh, C–C and Kirsch, G.E., "Mutational Analysis of Ion Conduction and Drug Binding Sites in the Inner Mouth of Voltage–Gated K+ Channels," *Biophys. Journal 67*:2316–2325 (1994).

Lopez, G.A., et al., "Evidence that the S6 segment of the Shaker voltage–gated K+ channel comprises part of the pore," *Nature 367*:179–182 (1994).

Taglialatela, M., et al., "Comparison of $H_5$, $S_6$, and $H_5$–$S_6$ Exchanges on Pore Properties of Voltage–dependent K+ Channels," *J. Biol. Chem. 269*(19):13867–13873 (1994).

Chen, C. and Okayama, H., "High–Efficiency Transformation of Mammalian Cells by Plasmid DNA," *Mol. Cell Biol. 7*(8):2745–2752 (1987).

Weedon, W.S. and Doughty, H.W., "Diphenylsulphoneorthocarboxylic Acid and Related Compounds," *Am. Chem. J. 33*:386–430 (1905).

\* cited by examiner

FIG. 1

```
                    P                              S6
           430        440       450       460       470       480       490
           ▼          ▼         ▼         ▼         ▼         ▼         ▼
Shaker H4  SIPDAFWWAVVTMTTVGYGDMTPVGVWGKIVGSLCAIAGVLTIALPVPVIVSNFNYFYHRETDQEEM
rKv1.1     ---------------------S---------Y--TIG---------------------------EG---Q
rKv1.4     ---------------------------K--IT-G---------------------------EN---Q
Shab       ---E------GI---------IC--TTAL--VI-TV-C-C----VV----I--I---N--AE--KNQMRR-KA
rKv2.1     ---AS-----TI---------IY--KTLL-----G--C------V-----I--I---N--SE--KEQKR--KA
Shaw       ---LGL----L----------A--KTYI-MF---A---L------------------------AMY-SHTQARAKL
rKv3.1     N--IG-------------L--Y--QTWS-ML---A---L-----M------------------GMY-SLAMAKQKL
rKv3.4     N--IG-------------L--Y--KTWS-ML---A---L-----M------------------GMY-SLAMAKQKL
Shal       ---A---YTI--------L--V--ETIA------GV-SLS---V--------------------SRI--QNQRADKR
mKv4.1     ---A---YTI--------L--V--STIA---F--I-SLS---V--------------------SRI--QNQRADKR
rKv4.2     ---A---YTI--------L--V--KTIA---F--I-SLS---V--------------------SRI--QNQRADKR
```

PHARMACOLOGICAL MODULATORS OF VOLTAGE-GATED POTASSIUM ION CHANNELS

RELATED APPLICATION

This application claims the benefit of U.S. Provisional Application No. 60/073,482, filed on Feb. 3, 1998, entitled "Pharmacological Modulators of Voltage-Gated Potassium Ion Channels" the entire teachings of which are incorporated herein by reference.

GOVERNMENT SUPPORT

The invention was supported, in whole or in part, by grant NS 29693 from the National Institute of Health. The Government has certain rights in the invention.

BACKGROUND OF THE INVENTION

Cells maintain concentration gradients of certain ions across their membranes. For example, cells have a lower sodium ion concentration and a higher potassium ion concentration inside the cell than that outside the cell. The concentration gradient of ions across the cell membrane and the selective permeability of the membrane results in the negative resting potential of the cell. Voltage-gated ion channels open in response to a perturbation of the resting potential of the cell and allow ions to flow into or out of the cell in the direction of lower concentration.

Voltage-gated ion channels are involved in many cellular processes. For example, nerve cells maintain a negative resting potential when not transmitting an electrical impulse. When an excitatory synaptic signal occurs, depolarization causes voltage-gated sodium channels to open. Since the concentration of sodium ions outside the cell is much higher than that inside the cell, positively charged sodium ions flow into the cell causing a further depolarization of the cell membrane. Voltage-gated potassium ion channels, for example, Shaker class Kv1.x–Kv4.x channels, also open in response to depolarization and are responsible for restoring the cell to its resting potential. Since the potassium ion concentration inside the cell is higher than that outside the cell, the positively charged potassium ions flow out of the cell and bring the cell back to its resting potential.

Because voltage-gated potassium ion channels are responsible for returning neurons to their resting potential, agents that prolong the length of time that the channel remains open, or potentiate channel activity, are expected to be useful in treating disorders characterized by abnormally high electrical activity, such as seizures and cardiac arrhythmias. However, for the majority of voltage-gated potassium ion channels, there are no known compounds that prolong the opening of the channel. Conversely, agents that decrease the length of time that the channel remains open, or inhibit channel activity, are expected to be useful in treating disorders that are characterized by loss of conductivity in neurons, such as multiple sclerosis or demyelination due to injury.

In addition, the activation of voltage-gated potassium ion channels is involved in mediating the immune response to an antigen. Therefore, inhibitors of these channels are expected to be therapeutically useful in suppressing graft rejection by inhibiting the immune response, and potentiators are expected to help stimulate immune response in cases where it is pathologically depressed.

SUMMARY OF THE INVENTION

Reported herein is the discovery of an allosteric receptor site located on the intracellular surface of Shaker class voltage-gated potassium ion channels that is distinct from the channel pore. Shaker class voltage-gated potassium ion channels include the Kv1.x–Kv4.x channels. It has now been discovered that this allosteric regulatory site is involved in regulating gating of the pore. A class of compounds has been identified that binds to this allosteric site and modulates the length of time the channel pore remains open. Based on these discoveries, novel methods of modulating the activity of Shaker class voltage-gated potassium ion channels and assays for determining which compounds are modulators of these ion channels are reported herein.

In one embodiment, the invention relates to methods of modulating the activity of Shaker class voltage-gated potassium ion channels in a subject by administering an agent that binds to the allosteric site. The allosteric site in Shaker class voltage-gated potassium ion channels Kv1.x–Kv4.x is located on the intracellular surface and specifically affects channel gating and not ion permeation.

In another embodiment, the invention relates to a method of modulating the activity of Shaker class voltage-gated potassium ion channels in a subject by administering a compound that binds to a site in the Shaker class voltage-gated (I)

In structural formula I, X is —O—, —CO—, —S—, —SO— or —NH—.

Y is —(CH$_2$)$_n$—, or Y is absent. n is an integer from 0–2. When n=0, Y is a covalent bond.

Ring A is an unsubstituted aromatic group, or an aromatic group substituted with 1–5 substituents. Ring B is an aromatic group substituted with 1–5 substituents. Preferably, ring A and ring B are both phenyl, and R$^1$ is ortho or meta to "X".

R$^1$ is —(CHR$^2$)$_n$CO$_2$R$^2$.

R$^2$ is a hydrogen or a lower alkyl group. Preferably, R$^2$ is a hydrogen.

In another embodiment, the invention relates to an assay for determining whether a compound modulates Shaker class voltage gated potassium ion channels.

Compounds of this invention have potential therapeutic advantages because they do not modulate voltage-gated potassium channels unconditionally. In the presence of modulators of this invention, voltage-gated potassium ion channels respond normally to membrane depolarization by opening the ion channel. But once the channel is opened, modulators will increase or decrease the length of time the channels remain opened, thereby increasing or decreasing the activity of the ion channel. Therefore, modulators should not affect the resting excitability of a cell. Even at concentrations where the allosteric receptor site is saturated, modulators do not disrupt the normal opening of the channels and do not cause the severe reduction in current associated with ion channel-blockers. Instead, they merely retard or speed the closing of the channel. Therefore, the use of modulators of this invention potentially provides a therapeutically safe method of regulating potassium ion channel activity with minimal disruption of normal cellular processes.

DETAILED DESCRIPTION OF THE INVENTION

Figure 1:
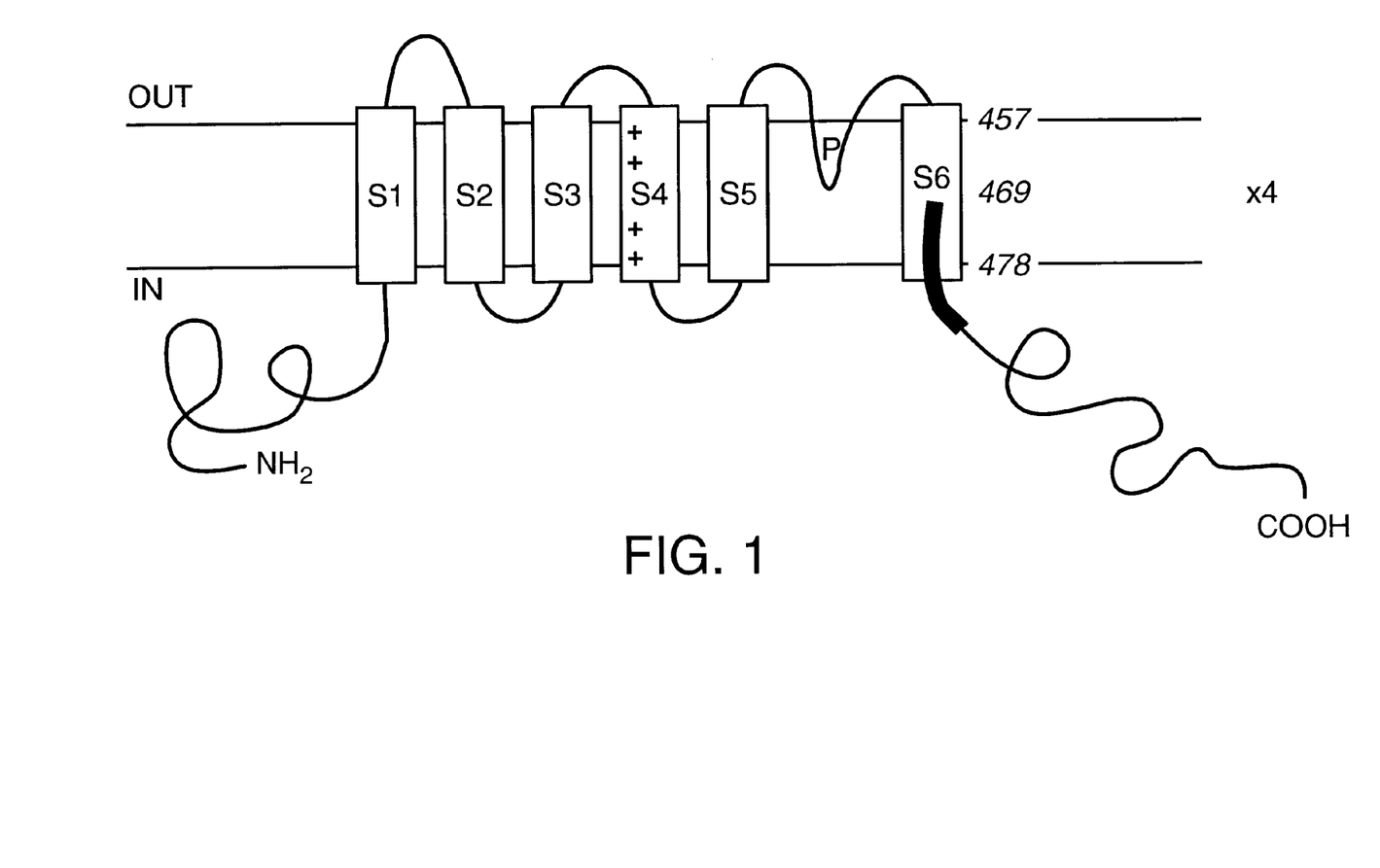
FIG. 1 is a schematic diagram of Drosophila Shaker H4 potassium ion channel spanning a cell membrane. The six hydrophobic membrane spanning regions of the channel are indicated in FIG. 1, the pore is indicated by a "P," and the amino acid residues of the S6 region are numbered.

The present invention is based on the discovery of an allosteric receptor site, that contains part of the S6 region of Shaker class voltage-gated potassium ion channels and is located on the intracellular side of the cell membrane, is involved in regulating gating of the pore. The "pore" as referred herein is the region of the ion channel through which potassium ions pass into and out of the cell and is indicated by a "P" in FIGS. 1 and 2. A class of compounds has been identified that binds to this allosteric site and modulates the length of time the channel remains open.

Figure 2:
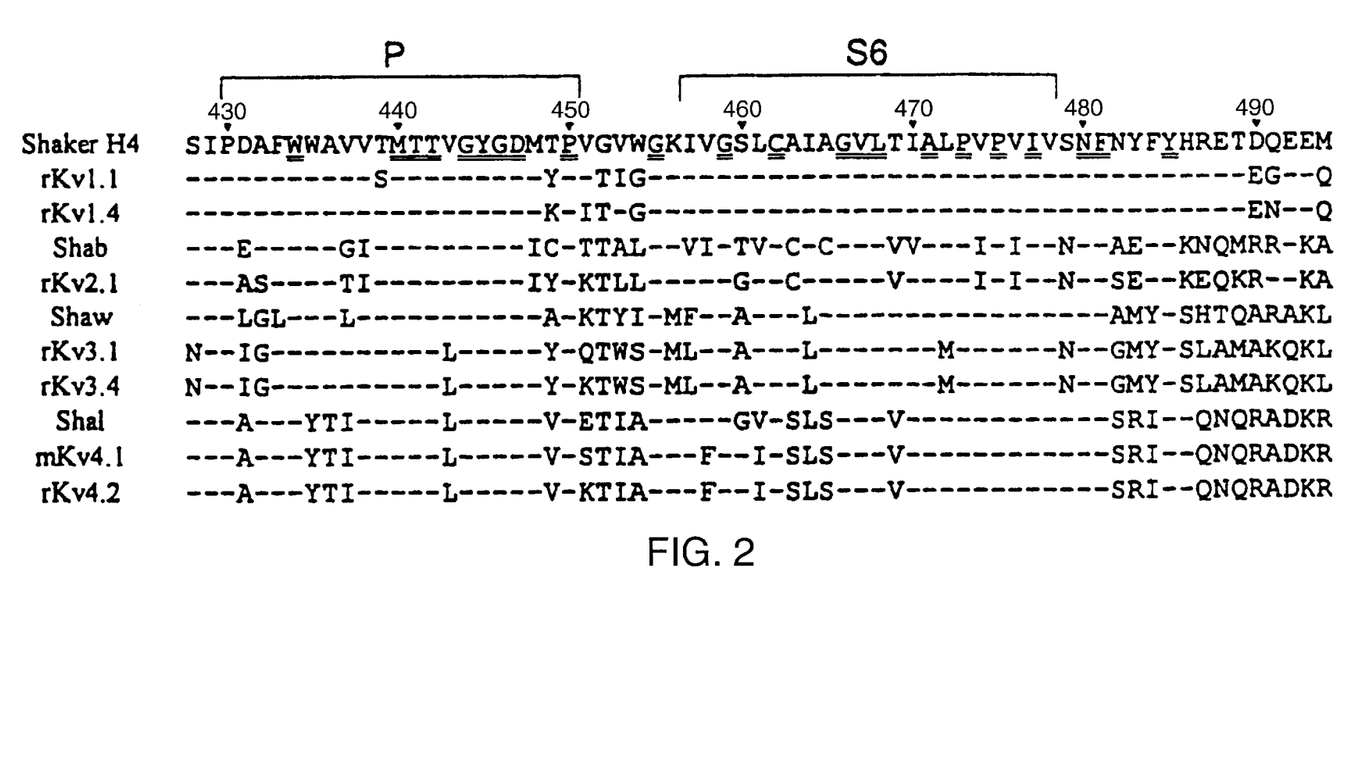
FIG. 2 is the amino acid sequence from related voltage-gated potassium channels of different families, showing the amino acid conservation in the P and the S6 regions. Dashes indicate residues that are the same as the corresponding Shaker H4 residue. Underscored residues are completely conserved in the Kv1.x–Kv4.x family. The numbering is that for the Shaker potassium channel.

Shaker class voltage-gated potassium ion channels are defined as the Kv1.x .x–Kv4.x channels and have amino acid sequences in the region of the pore and in the S6 region as shown in FIG. 2. They account for most of the voltage-gated potassium ion channels in nerve, muscle and secretory cells. For a more detailed discussion of Shaker class voltage-gated potassium ion channels see Choi, K. L., Mossman, C., Aube, J., and Yellen, G., *Neuron* (1993), 10:533; Shieh, C.-C. and Kirsch, G. E., *Biopkvs. Journal* (1994), 67:2316; Lopez, F. A., Jan, Y. N., and Jan, L. Y., *Nature* (1994), 367:179; Taglialatela, M., Champagne, M. S., Drewe, J. A., and Brown, A. M., *J. Biol. Chem.* (1994), 269:13867; Liu, Y.; Holmgren, M.; Jurman, M. E.; Yellen, G.; *Neuron*(1997), 19, 175; Chandy, K. G., Gutman, G. A., *Trends in pharmacological Sciences*(1993), 14:434; Chandy, K. G., Gutman, G. A., "Voltage-gated K+Channel Genes," *Handbook of Receptors and Channels: Ligand and Voltage-gated Ion Channels* (1995), A. North, ed. (CRC Press, Boca Raton, Fla.), p. 1–71.

The allosteric site reported herein is on the intracellular side of the cell membrane and is involved in regulating gating of the pore, but does not lie within the pore itself. Evidence that the allosteric site is involved in regulating gating of the pore is provided by the electrophysiology experiments in Example 4. These experiments demonstrate that the length of time a voltage-gated potassium ion channels remain open is increased or decreased in the presence of the compounds disclosed herein. The experiment in Example 5 demonstrates that compounds that are effective at the allosteric site do not compete with a known channel-blocker that binds within the pore. Channel-blockers are compounds that bind within the pore and cause a steady-state blockade of current through the pore. Experiment 5 provides evidence that the allosteric site is not within the pore. Finally, evidence that the allosteric site lies on the intracellular side of the cell membrane is provided by experiments disclosed in Example 6. These experiments demonstrate that 2-benzoylbenzoic acid, a compound that potentiates the activity of the ion channel, is effective only from the intracellular side of the cell membrane.

The allosteric site can alternatively be defined as the site in Shaker class voltage-gated potassium ion channels to which an exemplary compound of the invention, such as 2-benzoyl benzoic acid, binds.

Compounds of this invention are expected to be effective in treating disorders that involve nerve, muscle, and secretory cells. Potentiators can depress repetitive electrical activity because potassium ion channels are responsible for re-establishing the resting potential of a cell. Seizure disorders, such as epilepsy, and cardiac arrhythmias (including tachyarrhythmias, bradyarrhythmias, fibrillation, and long QT syndrome) where there is abnormally high electrical activity are expected to benefit by treatment with potentiators of this invention.

Conversely, inhibitors decrease the ability of potassium ion channels to re-establish the resting potential of a neuron, and therefore, allow the neuron to fire successive action potentials more rapidly. Disorder that cause a nerve conduction deficit, such as multiple sclerosis, white matter diseases, nerve injury, or autoimmune disorders that cause demyelination of neurons, are expected to benefit by treatment with inhibitors of this invention.

Other disorders of the nervous system that are expected to benefit from treatment with compounds of this invention include, but are not limited to, nerve degeneration, AIDS neuropathy, encephalomyclitis, sleep disorders, memory disorders, headache including migraine, hyperactivity, movement disorders, and comas.

Psychiatric disorders expected to benefit from treatment with the disclosed compounds are Alzheimer's disease, attentional disorders, bipolar disease, and psychosis.

Diseases that involve electrical dysfunction of the nerves or muscles, for example, paralysis, myotonia, spasticity, or chronic pain can also be treated with compounds disclosed herein.

Voltage-gated potassium ion channels have been shown to regulate the proliferation response of T cells to an antigen, therefore, compounds of this invention would be expected to modulate this response. Potentiators would be useful in treating conditions where the immune system is pathologically depressed due to a deficiency in antigen-induced lymphocyte proliferation, for example, AIDS. Inhibitors would be therapeutically useful in suppressing both allograph and xenograft rejection.

Disorders of the endocrine cells can also be treated with the compounds disclosed herein. Examples include diabetes, hyperinsulinemia, adrenal insufficiency or hypersecretion.

An "effective amount" is the quantity of the compound which results in the desired improved clinical outcome as a result of treatment compared with a typical clinical outcome in the absence of treatment. Alternatively, an "improved clinical outcome" includes a longer life expectancy for subjects with the disease as a result of treatment or results in the subject with the disease experiencing fewer symptoms or complications of the disease as a result of treatment. With respect to epilepsy, an "improved clinical outcome" includes fewer seizures or seizures of shorter duration.

With respect to demyelination disorders, for example, multiple sclerosis, an "improved clinical outcome" includes improved mobility.

With respect to graft rejection, an "improved clinical outcome" includes a longer life expectancy. Alternatively, it can include fewer complications due to graft rejection.

The amount of a compound administered to a subject will depend on the type and severity of the disease and on the characteristics of the subject, such as general health, age, sex, body weight and tolerance to drugs. It will also depend on the degree, severity and type of disease. The skilled artisan will be able to determine appropriate dosages depending on these and other factors. Typically, in human subjects, an effective amount of the compound can range from about 0.1 mg per day to about 100 mg per day for an adult. Preferably, the dosage ranges from about 1 mg per day to about 100 mg per day.

The compound can be administered by any suitable route, including, for example, orally in capsules, suspensions or tablets or by parenteral administration. Parenteral administration can include, for example, systemic administration, such as by intramuscular, intravenous, subcutaneous, or intraperitoneal injection. The compound can also be administered orally (e.g., dietary), topically, by inhalation (e.g., intrabronchial, intranasal, oral inhalation or intranasal drops), or rectally, depending on the disease or condition to be treated. Oral or parenteral administration are preferred modes of administration.

The compound can be administered to the individual in conjunction with an acceptable pharmaceutical carrier as part of a pharmaceutical composition. Formulation of a compound to be administered will vary according to the route of administration selected (e.g., solution, emulsion, capsule). Suitable pharmaceutical carriers may contain inert ingredients which do not interact with the compound. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringcer's-lactate and the like. Methods for encapsulating compositions (such as in a coating of hard gelatin or cyclodextran) are known in the art (Baker, et al., "Controlled Release of Biological Active Agents", John Wiley and Sons, 1986).

A "subject" is preferably a mammal, such as a human, but can also be an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like).

Agents that modulate the activity of Shaker class voltage-gated potassium ion channels by binding to the allosteric site are represented by structural formula I:

(I)

In structural formula I, X is —O—, —CO—, —S—, —SO— or —NH—.

Y is —$(CH_2)_n$—, or Y is absent. n is an integer from 0–2. When n=0, Y is a covalent bond.

Ring A is an unsubstituted aromatic group, or an aromatic group substituted with one or more substituents. Ring B is an aromatic group substituted with one or more substitutents. Preferably, ring A and ring B are both phenyl, and $R^1$ is ortho or meta to "X".

$R^1$ is —$(CHR^2)_n CO_2R^2$.

$R^2$ is a hydrogen or a lower alkyl group. Preferably, $R^2$ is a hydrogen.

When Y is absent, the modulators are represented by structural formula II:

(II)

In structural formula II, X, $R^1$, and the A and B rings are defined as above.

In a preferred embodiment, compounds that modulate the activity of Shaker class voltage-gated potassium ion channels by binding to the allosteric site are represented by structural formula III:

(III)

In structural formula III, X, and $R^2$ are defined as above. Ring A is unsubstituted or substituted with 1–5 substiutents, and ring B is optionally substituted with 1–3 substitutents in addition to —$NO^2$ and —$COOR^2$.

In another preferred embodiment, compounds that modulate the activity of Shaker class voltage-gated potassium ion channels by binding to the allosteric site are represented by structural formula IV:

(IV)

In structural formula IV, X and $R^2$ are defined as above. Ring A is unsubstituted or substituted with 1–5 substiutents, and ring B is optionally substituted with 1–3 substitutents in addition to —$R^3$ and —$COOR^2$.

Also included in the present invention are physiologically acceptable salts of the compounds represented by Structural Formulas I through IV. Salts of compounds containing a carboxylic acid can be prepared by reacting with a suitable base, for example, a hydroxide base. Salts of acidic functional groups contain a counteraction such as sodium, potassium and the like.

Compounds that modulate the activity of Shaker class voltage-gated potassium ion channels either potentiate or inhibit ion channel activity. Potentiators increase the activity of potassium ion channels by increasing the length of time that the channel remains open. Potentiators are represented by structural formula I, wherein X is generally —O—, —CO—, —S— or —SO—; Y, $R^1$, and rings A and B are defined as above.

Compounds that modulate the activity of Shaker class voltage-gated potassium ion channels can also be inhibitors of ion channel activity. Inhibitors are compounds that decrease the activity of voltage-gated potassium ion channels by decreasing the length of time that the channel remains open. Inhibitors are represented by structural formula I, wherein X is generally —NH—; Y, $R^1$, and the A and the B rings are defined as above.

Another embodiment includes pharmaceutical compositions comprising compounds represented by structural formulas I–IV and a suitable pharmaceutical carrier.

Another embodiment refers to novel compounds that modulate the activity of Shaker class voltage-gated potassium ion channels.

Suitable substituents for the A and B rings include an aryl group (including a carbocyclic aryl group or a heteroaryl group), a substituted aryl group, aliphatic groups, substituted aliphatic groups, hydroxy, —$OR^4$, —CHO, —$COR^4$, —$COOR^4$, —$NHCOR^4$, —$OCOR^4$, benzyl, halogenated lower alkyl (e.g., trifluoromethyl and trichloromethyl), halogens, cyano, nitro, —$SO_3^-$, —SH, —$SR^4$, —$NH_2$, —$NHR^4$, —$NR^4R^5$, or —COOH, wherein $R^4$ and $R^5$ are each, independently, an aliphatic group, a substituted aliphatic group, an aryl group, a substituted aryl group, an aralky group and a substituted aralkyl group.

Suitable electron donating groups include a —$NH_2$, —$NHR^4$, —$NR^4R^5$, —$OR^4$, —$SR^4$, —$NHCOR^4$, —$OCOR^4$, —OH, and —SH.

As used herein, aliphatic groups include straight chained, branched or cyclic $C_1$–$C_8$ hydrocarbons which are completely saturated or which contain one or more units of unsaturation. A "lower alkyl group" is a saturated aliphatic group having form 1–4 carbon atoms.

Aromatic groups include carbocyclic ring systems (e.g. benzyl and cinnamyl) and fused polycyclic aromatic ring systems (e.g. naphthyl and 1,2,3,4-tetrahydronaphthyl). In addition, aromatic groups includes heteroaryl ring systems (e.g. pyridines, thiophenes, furans, pyrroles, imidazoles, pyrazoles, triazoles, pyrimidines and pyrazines) and heteroaryl ring systems in which a carbocyclic aromatic ring, carbocyclic non-aromatic ring or heteroaryl ring is fused to one or more other heteroaryl rings (e.g. benzimidazole, indole, tetrahydroindole, azaindole, indazole and quinoline). An aryl group, as used herein, refer to an aromatic group having five or six atoms. An aralkyl group is an aryl substituent that is linked to a compound by an aliphatic group having from one to six carbon atoms.

"Substituted aliphatic groups," "substituted aryl groups," and "substituted aralkyl groups," can have one or more substituents. Suitable substituents for these groups are halogens, —COOH, cyano, nitro, alcohol, —$OR_4$, —SH, —$SR_4$, —$NH_2$, —$NHR_4$, and —$NR_4R_5$.

Competition between two active agents indicates that they act at similar or overlapping sites in the target protein. Competition, defined standardly by pharmacologists, involves an increase in the half-effective concentration for one active agent in the presence of another. Thus, an increase of half-effective concentration for a test compound in the presence of an exemplary compound, or for an exemplary compound in the presence of a test compound, is evidence for a competitive interaction between the two.

A specific example of such a test would be to use an exemplary compound that binds to the site but has a "neutral" allosteric interaction on the Shaker class voltage-gated potassium ion channel used for the test—i.e. minimal effects on activity. For the purpose of this test, activity refers either to the time constant for activation or to the time constant for deactivation of a Shaker class voltage-gated potassium ion channel. For example, the time constant for activation refers to the amount of time a Shaker class voltage-gated potassium ion channel remains open in response to a predetermined voltage stimulus. The exemplary compound would compete with a test compound acting at the allosteric site, increasing the concentration required for a given effect, but it should not show this interaction with a compound acting elsewhere. A similar test can be done with exemplary compounds that arc potentiators or inhibitors.

An exemplary compound should have a binding affinity of 100 mM for the allosteric site of Shaker class voltage-gated potassium ion channels. The binding affinity of a compound can be measured by placing a membrane containing a known amount of Shaker class voltage-gated potassium ion channels in one compartment of an equilibrium dialysis chamber. A solution having a known concentration of the radiolabeled exemplary compound is placed in a second compartment that is separated from the first compartment by a membrane which is permeable to the exemplary compound but is not permeable to the membrane containing the Shaker class voltage-gated potassium ion channels. When the system has reached equilibrium (ie., the concentration of the exemplary compound in each compartment remains constant), the concentration of the exemplary compound in each compartment is measured. The binding affinity can be determined by plotting the data using a Scatchard plot (see I. H. Segel, Biochemical Calculations, $2^{nd}$ Edition (1968), John Wiley & Sons, Inc., 241–244)

Competition can also be determined by the displacement of a radioactive exemplar compound by a test compound. Displacement can be monitored by a decrease in radioactivity of the cell membrane as the non-radioactive test compound displaces the exemplar compound from the allosteric site. Radioactivity of the cell membrane can be measured by any suitable means, for example, by a scintillation counter.

The invention is illustrated by the following examples, which are not intended to be limiting in any way.

EXEMPLIFICATION

Example 1

Chemical Synthesis

Synthesis of 2-Benzoyl-4-Nitroanthranilic Acid

Methods of synthesizing 2-benzoyl-4-nitroanthranilic acid are known to those in the art. Examples of syntheses of 2-benzoyl-4-nitroanthranilic acid can be found in the following references: Rainer, *Moiiatsh. Chem.* (1908), 29:178; Chardonnens, H., *Helv. Chim. Acta*(1944), 27:321; Kliegl, *Chem. Ber.* (1905), 38:294; Fahmy et al., *Indian J. Chem. Sect.* B (1977), 15:252; Noycc, Kittle, *J. Org. Chem.* (1967), 32:2459.

Synthesis of 2-Phenoxy-4-Nitroanthranilic Acid

2-Chloro-4-nitroanthranilic acid (40.2 g, 0.2 mol) is stirred in nitrobenzene (250 mL) with 3-nitrophenol (31 g, 0.22 mol), potassium carbonate (42 g, 0.3 mole), copper bronze (1 g) and cuprous iodide (1 g) at 155° C. for 6 hours. The pure product is obtained by recrystallization in ethyl alcohol to give 2-phenoxy-4-nitroanthranilic acid. (See Goldberg, Walker, *J. Chem. Soc.* (1953), 1348).

Synthesis of 2-Anilinobenzoic Acid

2-Bromotoluene (2 mmol) is heated to 230° C. for 6 hours with aniline (20 mmol) in the presence of $[(C_6H_5)_2PCH_2]_2Ni(CO)_2$ (0.2 mmol) using ethanol (1.2 mL) as the solvent in a sealed tube to form 2-anilinotoluene. 2-Anilinotoluene is oxidized with potassium permaganate in water to form 2-anilinobenzoic acid. (See Cramer, et al., *J. Org. Chem.* (1975), 40:2267).

Synthesis of 3-Nitro-6-Carboxydiphenyl Sulfide

Methods of synthesizing 3-nitro-6-carboxydiphenyl sulfide are known to those skilled in the art. An example of a synthesis of 3-nitro-6-carboxydiphenyl sulfide can be found in the following reference: Mayer, F., *Chem. Ber.* (1909), 42:3066.

Synthesis of 2-Carboxy-5-Nitro-4'-Methyldiphenyl Sulfide

The sodium derivative of 2-thio-5-methylmethylbenzoate (6–7 g) is mixed with 3-chloronitrobenzene (14 g) and heated to 165° C. for 2 hours. The mixture was cooled and acidified with Hcl, then steam distilled to remove the 3-chloronitrobenzene. The product is purified by recrystallization from methanol to give 2-carbomethoxy-5-nitro-4'-methyldiphenyl sulfide. The ester is then hydrolyzed by boiling it with N-potassium hydroxide (110 mL) for 2 hours. The product is recrystallized from toluene to give 2-carboxy-5-nitro-4'-methyldiphenyl sulfide. (See Mann, Turnbull, *J. Chem. Soc.* (1951), 747).

Synthesis of 2-Carboxydiphenyl Sulfoxide

Anthranilic acid (41.0 g, 300 mmol) is dissolved in 200 mL of water, then 64 mL of HCl is added. The solution is cooled to 0° C. and diazotized with a solution of $NaNO_2$ (22 g, 319 mmol) in 45 mL of water. The diazonium salt solution is stirred at 0° C. for 30 min. and then is kept at 0° C. while it is added dropwise during the course of 2.5 hours to a rapidly stirring, 0° C. solution of thiophenol (34.0 g, 309 mmol) in 300 mL of water containing 60 g (1500 mmol) of NaOH and 3 g of copper powder. Caution is exercised during the addition because of the explosive nature of diazo sulfide which can accumulate during addition. The mixture is stirred at 0° C. for 1 hour, allowed to warm to 25° C. overnight and then heated in a steam bath for 1 hour. The mixture is cooled and the solid is removed by filtration and washed with 200 mL of cold water. The combined filtrates are acidified with concentrated HCl, and the brown precipitate is collected and recrystallized successively with ethanol, ethanol-water (3:2) and benzene-hexane to give 2-carboxydiphenyl sulfide. 2-Carboxydiphenyl sulfide is dissolved in 100 mL of methanol and chilled to 0° C., then poured into a 100 mL of aqueous 0.51 M sodium metaperiodate at 0° C. The mixture is stirred overnight, then the solvent is evaporated. The solid residue is washed with water and recrystallized from ethanol-water to give 2-carboxydiphenyl sulfoxide. Other examples of the synthesis of 2-carboxydiphenyl sulfoxide can be found in the following references: Mayer, F., *Chem. Ber.* (1909), 42:3047; Weedon, et al., *Am. Chem. J.* (1905), 33:392–402; Brannigan, et al., *J Med. Chem.* (1976), 19:798; Livant, Martin, *J. Am. Chem. Soc.* (1977), 99:5761; Brown, et al., *J. Chem. Soc. Perkin Trans. I*(1972), 2842; Dhareshwar, Hosangadi, *Indian J. Chem. Sec. B* (1978), 16:143.

Synthesis of 2-Carboxy-5-Nitrodiphenyl Sulfoxide

2-Carboxydiphenyl sulfide (10 g) is placed in a flask and 20 mL of fuming nitric acid is added slowly. Once the first violent reaction has subsided, the mixture is refluxed for 3 hours, then cooled and poured into water. The sticky yellow solid that separates from the water is recrystallized from benzene to give 2-carboxy-5-nitrodiphenyl sulfoxide. (See Weedon, et al., *Am. Chem. J.*(1905), 33:394).

Example 2

Mutagenesis and Expression

Cloned Shaker potassium channels were transiently expressed in HEK293 cells. Methods for mutagenesis have been described previously (see *Current Protocols in Molecular Biology*(1992), Ed. Ausubel, F. M., Brent, R., Kingston, R. E., Moore, D. D., Seidman, J. G., Smith, J. A., Struhl, K., John Wiley & Sons the entire teachings of which are incorporated herein by reference) Cysteine was substituted at an individual position in the protein to serve as a monitor of chemical modification. This was done by mutation of the cDNA sequence. The desired new DNA sequence was planned, substituting a cysteine codon at the target position. Oligonucleotides of 20–30 bases in length, corresponding to the forward, coding sequence and reverse, complementary sequence were prepared. These oligonucleotides were used in a series of polymerase chain reaction to produce a fragment of the channel cDNA that contains the new coding sequence. This fragment was then subcloned at the appropriate position into the cDNA expression plasmid.

A variety of standard methods for mutagenesis are equally applicable.

Example 3

Expression of Shaker H4 Ion Channels in HEK293 Cells

Materials

Magnetic polystyrene microspheres, precoated with anti-CD8 antibody, were purchased from Dynal (Dynalbeads® M-450 CD8; Great Neck, N.Y., USA). The beads were supplied at a concentration of $1-4\times10^8$/mL and were resuspended by mixing before use.

Plasmid Expression Vectors

The expression plasmid pH3-CD8 for the a subunit of the human CD8 lymphocyte surface antigen contains the CDNA for the CD8 a subunit (GenBank® M12824) under the control of the human cytomegalovirus (hereinafter "CMV") promoter. The expression plasmid for Shaker potassium channels GW1-ShIR contains CDNA for the Shaker H4 channel from Drosophila. Amino acids 6–46 have been deleted to remove rapid channel inactivation, and the cDNA is expressed under the control of a CMV promoter. The simian virus 40 (hereinafter "SV40") T-antigen plasmid expresses the large T antigen under control of the viral promoter.

Cell Culture

HEK 293 cells were obtained from ATCC (Rockville, Md., USA). They were grown in DMEM-F12 medium (JRH Scientific, Lenexa, Kans., USA) supplemented with 10% fetal bovine serum (Life Technologics, Gaithersburg, Md., USA).

Electroporation

One to three days prior to transfection, cells at 40%–60% confluence were trypsinized and plated in 75-cm$^2$ tissue culture flasks. On the day of transfection, cells at 50%–70% confluence were trypsinized, washed once with HEPES-buffered saline (HBS=140 mM NaCl. 25 mM HEPES, 1.6 mM Na$_2$HPO$_4$pH 7.4) and resuspended in HBS at 2×10$^6$ cells/mL. The cells were placed on ice for 20 min. for each electroporation. 200 mL of the cell suspension were transferred to a 0.4-cm electroporation cuvette and mixed with plasmid DNA as follows: 25 mg Shaker K$^+$channel, 5 mg CD8 and 1 mg SV40 T-antigen plasmid. The cell/DNA mixture was then placed on ice for 2 min. All of the expression plasmids contain the SV40 origin of replication.

The settings of the Invitrogen ElectroPorator™ (San Diego, Calif., USA) were capacitance equal to 71 mF and load resistance of infinity. For these experiments the output voltage of the Pharmacia Biotech ECPS 3000/150 power supply (Piscataway, N.J., USA) was set to 330 V. Following electroporation, the cells were put back on ice for 2 min. and then transferred to 35-mm dishes containing growth media and protamine-treated glass coverslips.

Calcium Phosphate Transfection

HEK293 cells were alternatively transfected by co-precipitation with CaPO$_4$ according to the method of Chen, C. and Okayama, H., *Mol. Cell Biol.* 1987, 7, 2745. One day prior to transfection, cells were plated at 30% confluence in 100-mm tissue culture dishes. On the morning of transfections the media were changed, and 6 h later each dish received 0.1 volume of BES-buffered saline (50 mM BES, 280 mM NaCl, 1.5 mM NaHPO$_4$, pH 6.96) containing 250 mM CaCl$_2$ and the following expression plasmid DNA's: 5 μg CD8 and 1 μg SV40T. Cells were kept in a humidified incubator at 37° C. and 3% CO$_2$. A fine DNA/CaPO$_4$ co-precipitate formed overnight. The following morning, the cells were washed and replenished with fresh media and placed in an incubator at 5% CO$_2$.

Decoration of Transfected Cells with Beads

95% of successfully transfected cells expressed both the human CD8 lymphocyte surface antigen and Drosophila Shaker H4 potassium channels. On the day of use, culture medium was removed from the cells and replaced with a saline solution (155 mM NaCl, 5 mM KCl, 3 mM CaCl$_2$, 1 mM MgCl$_2$, 10 mM HEPES, pH 7.4) containing 0.5% bovine serum albumin and a 1:1000 dilution of beads precoated with anti-CD8 antibody. A volume of 1–2 mL was used for a 35-mm culture dish. After 1–5 min. of incubation at room temperature, with occasional agitation, the excess beads were removed by rinsing with saline. Cells that had CD8 receptors, and hence Shaker H4 potassium ion channels, retained some of the beads allowing them to be identified visually in the microscope. The cells were rinsed with saline, and at this point, could be used for physiology recordings.

Example 4

Physiological Recording

Standard patch recording methods were used to record potassium channel currents from the transfected cells (Hamill, O. P., Marty, A., Neher, E., Sakmann, B., and Sigworth, F. J., *Pfluegers Arch*(1981), 391:85, the entire teachings of which are incorporated herein by reference). If expression was sufficiently high, the excised inside-out or excised outside-out recording configurations was used; otherwise the whole cell recording configuration was used. Typically, compounds were applied to the intracellular surface of an inside-out patch. Standard extracellular saline was used in the recording pipette, and standard intracellular saline was perfused on the exposed side, or bath side, of the membrane. Test compounds were added to the intracellular saline at the concentration specified.

For recording the time course of channel activation and deactivation, voltage clamp steps were applied from a resting potential of −80 to −100 mV to an activation potential of between −60 and +60 mV; after these activating steps (lasting 5–100 ms in duration), the voltage was returned to a potential of between −120 and −60 mV to monitor the time course of closure, or de-activation, of the channels. Standard experimental solutions contained, in mM: 150 NaCl, 10 KCl, 3 CaCl$_2$, 1 MgCl$_2$, and 10 HEPES, at pH 7.4 in the pipette solution; and 160 KCl, 0.5 MgCl$_2$, 1 EGTA, and 10 HEPES, at pH 7.4 in the bath solution. Solutions with Cd$^{2+}$ contained no EGTA.

In Table I, II and III, the time course of closure of Drosophila Shaker H4 potassium ion channels was measured in the presence of a test compound and compared to the time course of closure in the absence of a test compound. In the case of 2-benzoylbenzoic acid the same experiment was also performed using rat Kv1.x.4 potassium ion channel expressed in HEK293 cells with similar result as those for Drosophila Shaker H4 ion channels.

TABLE 1

Potentiators of Shaker class voltage-gated potassium ion channels

| Example | Test Compound (0.5 mM) | Approximate Increase in Time Course of Closure | Commercial Supplier |
| --- | --- | --- | --- |
| 1 | 2-benzoylbenzoic acid | 2.5 X | Aldrich |
| 2 | 2-(3-amino-4-chlorobenzoyl)benzoic acid | 2 X | Aldrich |
| 3 | 2-(4-chloro-3-nitrobenzoyl)benzoic acid | 2 X | |
| 4 | 2-(4-chlorobenzoyl)benzoic acid | 2 X | Aldrich |
| 5 | 2-aminobenzophenone-2-carboxylic | 2 X | Aldrich |
| 6 | 2-(p-toluoyl)benzoic | 2 X | Aldrich |
| 7 | 2-phenoxybenzoic | 2 X | Aldrich |

TABLE 1-continued

Potentiators of Shaker class voltage-gated potassium ion channels

| Example | Test Compound (0.5 mM) | Approximate Increase in Time Course of Closure | Commercial Supplier |
|---|---|---|---|
| 8 | 4-nitro-4'-acetamide-2,2'-disulfonate stilbene | 2 X | |
| 9 | 4-nitro-2-(3-nitrophenoxy)benzoic acid | >5 X | Sigma, Aldrich, Maybridge |
| 10 | fenoprofen | 2.2 X | |
| 11 | ketoprofen | 2.3 X | |
| 12 | niflumic acid | 2.4 X | Aldrich |
| 13 | 4,4'-diamino-2,2'-disulfonate stilbene | 2 X | |
| 14 | 4,4'-dinitro-2,2'-disulfonate stilbene | 1.4 X | |
| 15 | 2-(4-amino-3-nitro-benzoyl)benzoic acid | ≧2 X | Maybridge |
| 16 | 2-(4-methoxyphenoxy)-3-nitrobenzoic acid | 1.5 X | Maybridge |
| 17 | 2-(3-methoxyphenoxy)-3-methoxybenzoic acid | <2 X | Maybridge |
| 18 | 2-sulfamide-4-methyl-2'-carboxydiphenyl sulfide | <2 X | Maybridge |
| 19 | 1-carboxydiphenyl sulfoxide | 2.2 X | Maybridge |
| 20 | 2-(4-chlorophenoxy)-3-aminobenzoic acid | 9X | Maybridge |
| 21 | 2-(3-nitrophenoxy)benzoic acid | 3–4 X | Maybridge |
| 22 | 2-(4-methylbenzoyl)benzoic acid | 2 X | Aldrich-Sigma |

TABLE 2

Inhibitors of Shaker class voltage-gated potassium ion channels

| Example | Test Compound (0.5 mM) | Approximate Decrease in Time Course of Closure | Commercial Supplier |
|---|---|---|---|
| 1 | 4-methoxy-2-(3-methoxy-benzoyl)-benzoic acid | ≦2 X | Maybridge |
| 2 | 2-(4-dibutylamino-2-hydroxybenzoyl) benzoic acid | 6.4 X | Aldrich |
| 3 | N-(2-amino-4-chlorophenyl) anthranilic acid | 2.4 X | Aldrich |
| 4 | Meclofenamic acid | 2.5 X | |
| 5 | Carprofen | 3.2 X | |
| 6 | N-(4-ethoxyphenyl)-4-nitro anthranilic acid | 5–10 X | |
| 7 | 2-benzoyl-3,4,5,6-tetrachloro-benzoic | ≧2 X | Aldrich-Sigma |
| 11 | 4-bromo-2-(phenoxy) benzoic acid | ≧2 X | Aldrich-Sigma |
| 12 | 2-(2,3,4,5,6-pentamethylbenzoyl) benzoic acid | 2 X | Maybridge |

TABLE 3

Compounds that have no effect on Shaker class voltage-gated potassium ion channels

| Example | Compound |
|---|---|
| 1 | 3-benzoyl benzoic acid |
| 2 | 4-benzoyl benzoic acid |
| 3 | 4-(4-(2-carboxybenzoyl)phenyl)butyric |
| 4 | 3-phenoxybenzoic |
| 5 | 2-2'-oxydibenzoic acid |
| 6 | 5-(4-carboxy-2-nitrophenyl)isophalic |
| 7 | N-phenylanthranilic |
| 8 | 2,2'-iminodibenzoic acid |
| 9 | Mefenamic acid |
| 10 | Flufenamic acid |
| 11 | Tolefenamic acid |

Discussion

Figure 3:
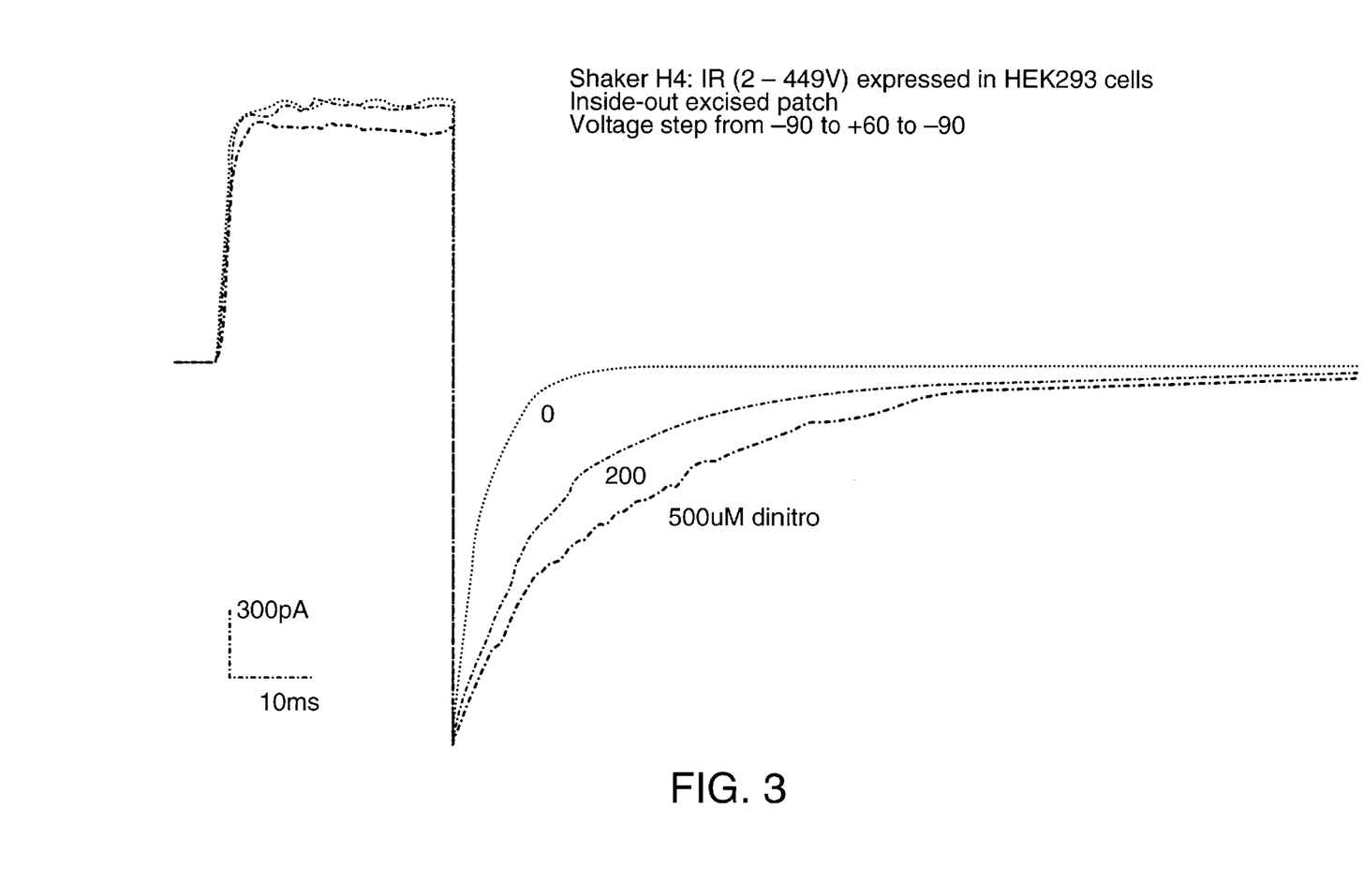
FIG. 3 is an example of an electrophysiology experiment showing the record of an inside-out excised patch voltage clamp current of a potassium ion channel in the presence or absence of 2-(3-nitrophenoxy)-4-nitroanthranilic acid at the concentrations shown. The experiment shows that the compound has little or no effect on the maximal level of outward or the inward current, and the compound slows the closing of the ion channel.
Figure 4:
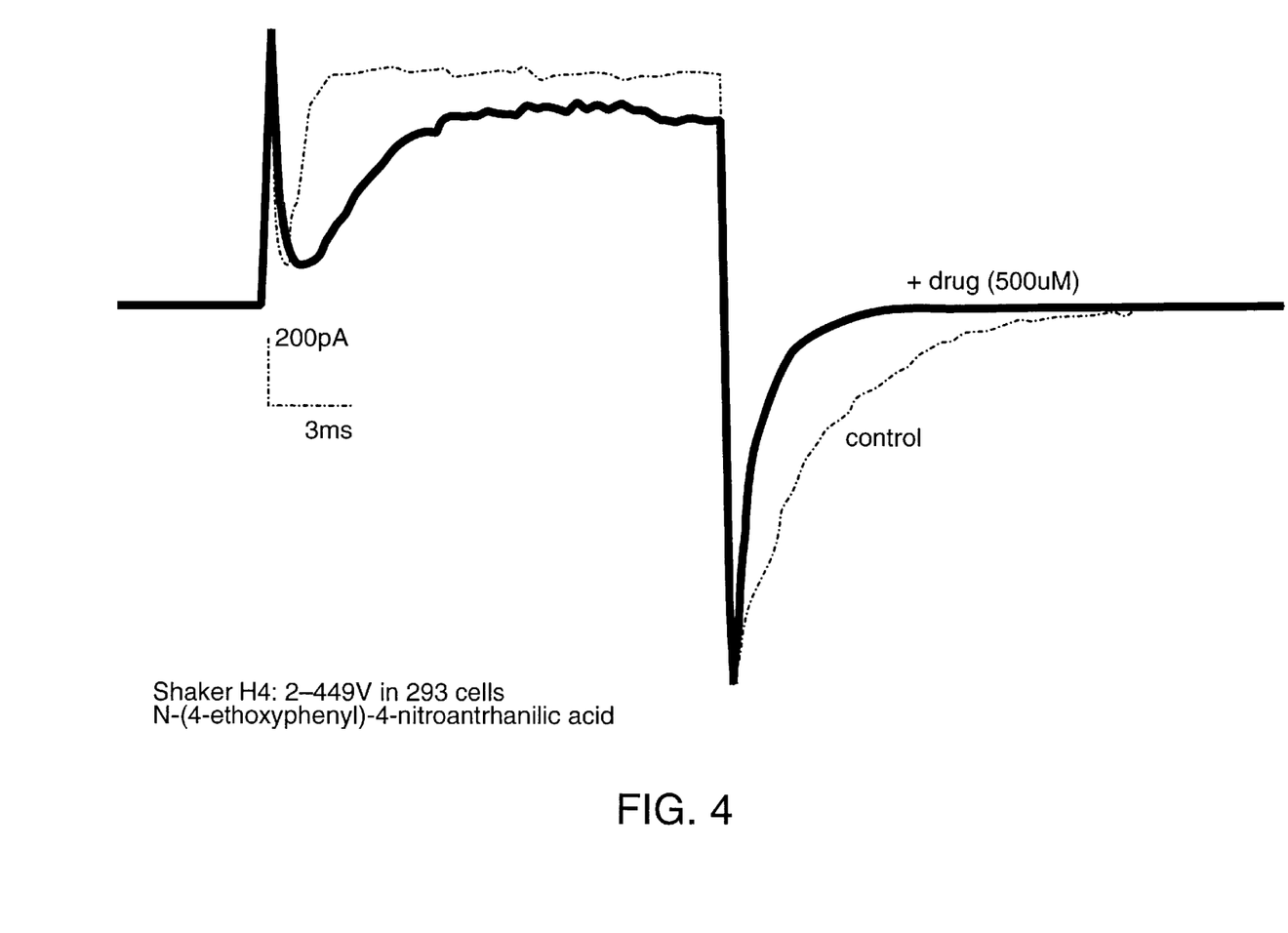
FIG. 4 is an example of an electrophysiology experiment showing the record of an inside-out excised patch voltage clamp current of a potassium ion channel in the presence or absence of N-(4-ethoxyphenyl)-4-nitroanthranilic acid at the concentrations shown. The experiment shows that there is less than a 20% reduction in the maximal level of outward or the inward current, and the compound speeds the closing of the ion channel.

The experimental data in Tables I–III, which was obtained from inside-out excised patch voltage clamp experiments similar to the one shown in FIG. 3 and 4, demonstrates that the compounds of the invention increase or decrease the length of time the channel remains open but do not eliminate current through the pore. Compounds that bind within the pore generally occlude the pore, and thus, prevent electrical current in the form of potassium ion movement through the pore. This is true for a large number of channel-blockers. Therefore, these experiments demonstrate that the allosteric site is not within the pore itself.

Example 5

Electrophysiology Experiments in the Presence of Channel-Blockers

At a depolarizing pulse of +60 mV, the steady state blockade of current caused by channel-blockers was measured as the current in the presence of the channel-blocker divided by the current in the absence of the channel-blocker. The channel-blocker tetraethylammonium (5 mM) caused a 15% steady state blockade of current. In the presence of 10 mM 2-benzoylbenzoic acid, a compound that binds at the allosteric site and potentiates ion channel activity, the steady state blockade of current by tetraethylammonium (5 mM) was 16%.

Discussion

Compounds that bind within the pore should interfere with the ability of known channel-blockers, to effect potassium ion current. Therefore, compounds of this invention do not compete for a binding site within the pore with channel-blockers.

Example 6

Experiments Indicating that the Allosteric Site is on the Intracellular Side of the Membrane Some compounds of the invention are effective from only one side of the membrane (e.g. 2-benzoylbenzoic acid) because they are not hydrophobic enough to be sufficiently membrane-permeant. Compounds were applied to the intracellular side of the cell membrane by adding the compound to the solution bathing the exposed face of an excised inside-out patch containing Drosophila Shaker H4 potassium ion channels. Application to the extracellular side of the membrane was performed by adding the compound to the solution bathing the exposed face of an excised outside-out patch containing Drosophila Shaker H4 potassium ion channels.

Discussion

In those cases where the compounds were effective from only one side, they were effective only when they were applied to the intracellular side of the cell membrane. This indicates that the location of the allosteric site is on the intracellular side of the cell membrane.

EQUIVALENTS

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of modulating the activity of Shaker class voltage-gated potassium ion channels in a subject, comprising administering to the subject an effective amount of an agent that binds to an allosteric site on the intracellular side of the cell membrane that is not within the pore, wherein the agent does not eliminate current through the channel and does not compete with channel-blockers for binding.

2. A method of modulating the activity of Shaker class voltage-gated potassium ion channels in a subject, comprising administering to the subject an effective amount of an agent that binds to a site in Shaker class voltage-gated potassium ion channels, wherein the compound is represented by the following structural formula:

and physiologically acceptable salts thereof, wherein:
X is —O—, —CO—, —S—, —SO— or —NH—;
Y is —(CH$_2$)$_n$— or absent;
n is an integer 0–2;

ring A is an unsubstituted aromatic group or a substituted aromatic group having one or more substitutents;
ring B is an aromatic ring having one or more substitutents;
R$^1$ is —(CHR$^2$)$_p$CO$_2$R$^2$;
R$^2$ is hydrogen or a lower alkyl group; and
p is an integer from 0–1.

3. The method of claim 2 wherein the compound is selected from the group consisting of 2-benzoylbenzoic acid, 2-(3-nitrophenoxy)benzoic acid, 2-(4-dibutylamino-2-hydroxybenzoyl)benzoic acid and N-4-ethoxyphenyl)-4-nitro anthranilic acid.

4. The method of claim 1, wherein the agent is represented by the following structural formula:

and physiologically acceptable salts thereof, wherein:
X is —O—, —CO—, —S—, —SO— or —NH—;
Y is —(CH$_2$)$_n$— or absent;
n is an integer 0–2;

ring A is an unsubstituted aromatic group or a substituted aromatic group having one or more substitutents;

ring B is an aromatic ring having one or more substitutents;

$R^1$ is $-(CHR^2)_p CO_2 R^2$;

$R^2$ is hydrogen or a lower alkyl group; and p is an integer from 0–1.

5. The method of claim, 2, wherein X is —CO—.

6. The method of claim 2 wherein the compound is represented by the following structural formula:

7. The method of claim 2, wherein the compound is represented by the following structural formula:

8. The method of claim 2, wherein the compound is represented by the following structural formula:

wherein:
$R^3$ is an electron donating group.

9. The method of claim 2, wherein the potassium ion channel activity is enhanced.

10. The method of claim 9, wherein the agent is 2-(3-nitrophenoxy)-4-nitroanthranilic acid.

11. The method of claim 9, wherein the subject is in need of treatment for seizures.

12. The method of claim 9, wherein the subject is in need of treatment for cardiac arrhythmia.

13. The method of claim 9, wherein the subject is in need of treatment for a deficiency in antigen-induced lymphocyte proliferation.

14. The method of claim 9, wherein X is —O—, —CO—, —S—, or —SO—.

15. The method of claim 2, wherein potassium ion channel activity is inhibited.

16. The method of claim 15, wherein the subject is in need of treatment for a nerve conduction deficit.

17. The method of claim 16, wherein the nerve conduction deficit is caused by multiple sclerosis.

18. The method of claim 16, wherein the nerve conduction deficit is caused by injury to nerve cells.

19. The method of claim 15, wherein the subject is in need of treatment to prevent graft rejection.

20. The method of claim 19, wherein the graft is an organ graft.

21. The method of claim 20, wherein the organ graft is an allograft.

22. The method of claim 20, wherein the organ graft is a xenograft.

23. The method of claim 15, wherein X is —NH—.

* * * * *

UNITED STATES PATENT AND TRADEMARK OFFICE
CERTIFICATE OF CORRECTION

PATENT NO.   : 6,291,442 B1                                          Page 1 of 1
DATED        : September 18, 2001
INVENTOR(S)  : Gary I. Yellen It is certified that error appears in the above-identified patent and that said Letters Patent is hereby corrected as shown below:

<u>Column 26,</u>
Line 15, delete "nitroanthranilic" and add -- nitrobenzoic --

Signed and Sealed this

Fourteenth Day of May, 2002

Attest:

JAMES E. ROGAN
*Attesting Officer*                *Director of the United States Patent and Trademark Office*

SEQUENCE LISTING

<160> NUMBER OF SEQ ID NOS: 11

<210> SEQ ID NO 1
<211> LENGTH: 75
<212> TYPE: PRT
<213> ORGANISM: drosophila/melanogaster
<300> PUBLICATION INFORMATION:
<301> AUTHORS: Liu, T. et al.
<303> JOURNAL: Neuron
<304> VOLUME: 19
<306> PAGES: 175-184
<307> DATE: 1997-07-01

<400> SEQUENCE: 1

Ser His Ser Ile Pro Asp Ala Phe Trp Trp Ala Val Val Thr Met Thr
1               5                   10                  15

Thr Val Gly Tyr Gly Asp Met Thr Pro Val Gly Val Trp Gly Lys Ile
            20                  25                  30

Val Gly Ser Leu Cys Ala Ile Ala Gly Val Leu Thr Ile Ala Leu Pro
        35                  40                  45

Val Pro Val Ile Val Ser Asn Phe Asn Tyr Phe Tyr His Arg Glu Thr
    50                  55                  60

Asp Gln Glu Glu Met Ser Glu Gln Ile Asp Asn
65                  70                  75

<210> SEQ ID NO 2
<211> LENGTH: 68
<212> TYPE: PRT
<213> ORGANISM: Unknown
<220> FEATURE:
<223> OTHER INFORMATION: Potassium Ion channel
<300> PUBLICATION INFORMATION:
<301> AUTHORS: Liu, Y., et al.
<303> JOURNAL: Neuron
<304> VOLUME: 19
<306> PAGES: 175-184
<307> DATE: 1997-07-01

<400> SEQUENCE: 2

Lys Ser Ile Pro Asp Ala Phe Trp Trp Ala Val Val Ser Met Thr Thr
1               5                   10                  15

Val Gly Tyr Gly Asp Met Tyr Pro Val Thr Ile Gly Gly Lys Ile Val
            20                  25                  30

```
Gly Ser Leu Cys Ala Ile Ala Gly Val Leu Thr Ile Ala Leu Pro Val
         35                  40                  45

Pro Val Ile Val Ser Asn Phe Asn Tyr Phe Tyr His Arg Glu Thr Glu
     50                  55                  60

Gly Glu Glu Gln
65

<210> SEQ ID NO 3
<211> LENGTH: 68
<212> TYPE: PRT
<213> ORGANISM: Unknown
<220> FEATURE:
<223> OTHER INFORMATION: Potassium Ion channel
<300> PUBLICATION INFORMATION:
<301> AUTHORS: Liu, Y., et al.
<303> JOURNAL: Neuron
<304> VOLUME: 19
<306> PAGES: 175-184
<307> DATE: 1997-07-01

<400> SEQUENCE: 3

Lys Ser Ile Pro Asp Ala Phe Trp Trp Ala Val Val Thr Met Thr Thr
 1               5                  10                  15

Val Gly Tyr Gly Asp Met Lys Pro Ile Thr Val Gly Gly Lys Ile Val
             20                  25                  30

Gly Ser Leu Cys Ala Ile Ala Gly Val Leu Thr Ile Ala Leu Pro Val
         35                  40                  45

Pro Val Ile Val Ser Asn Phe Asn Tyr Phe Tyr His Arg Glu Thr Glu
     50                  55                  60

Asn Glu Glu Gln
65

<210> SEQ ID NO 4
<211> LENGTH: 67
<212> TYPE: PRT
<213> ORGANISM: Unknown
<220> FEATURE:
<223> OTHER INFORMATION: Potassium Ion channel
<300> PUBLICATION INFORMATION:
<301> AUTHORS: Liu, Y., et al.
<303> JOURNAL: Neuron
<304> VOLUME: 1997
<306> PAGES: 175-184
<307> DATE: 1997-07-01

<400> SEQUENCE: 4

Ser Ile Pro Glu Ala Phe Trp Trp Ala Gly Ile Thr Met Thr Thr Val
 1               5                  10                  15

Gly Tyr Gly Asp Ile Cys Pro Thr Thr Ala Leu Gly Lys Val Ile Gly
             20                  25                  30

Thr Val Cys Cys Ile Cys Gly Val Leu Val Val Ala Leu Pro Ile Pro
         35                  40                  45

Ile Ile Val Asn Asn Phe Ala Glu Phe Tyr Lys Asn Gln Met Arg Arg
     50                  55                  60

Glu Lys Ala
65

<210> SEQ ID NO 5
<211> LENGTH: 67
<212> TYPE: PRT
<213> ORGANISM: Unknown
<220> FEATURE:
<223> OTHER INFORMATION: Potassium Ion channel
```

```
<300> PUBLICATION INFORMATION:
<301> AUTHORS: Liu, Y., et al.
<303> JOURNAL: Neuron
<304> VOLUME: 19
<306> PAGES: 175-184
<307> DATE: 1997-07-01

<400> SEQUENCE: 5

Ser Ile Pro Ala Ser Phe Trp Trp Ala Thr Ile Thr Met Thr Thr Val
 1               5                  10                  15

Gly Tyr Gly Asp Ile Tyr Pro Lys Thr Leu Leu Gly Lys Ile Val Gly
                20                  25                  30

Gly Leu Cys Cys Ile Ala Gly Val Leu Val Ile Ala Leu Pro Ile Pro
                35                  40                  45

Ile Ile Val Asn Asn Phe Ser Glu Phe Tyr Lys Glu Gln Lys Arg Gln
        50                  55                  60

Glu Lys Ala
65

<210> SEQ ID NO 6
<211> LENGTH: 67
<212> TYPE: PRT
<213> ORGANISM: Unknown
<220> FEATURE:
<223> OTHER INFORMATION: Potassium Ion channel
<300> PUBLICATION INFORMATION:
<301> AUTHORS: Liu, Y., et al.
<303> JOURNAL: Neuron
<304> VOLUME: 19
<306> PAGES: 175-184
<307> DATE: 1997-07-01

<400> SEQUENCE: 6

Ser Ile Pro Leu Gly Leu Trp Trp Ala Leu Val Thr Met Thr Thr Val
 1               5                  10                  15

Gly Tyr Gly Asp Met Ala Pro Lys Thr Tyr Ile Gly Met Phe Val Gly
                20                  25                  30

Ala Leu Cys Ala Leu Ala Gly Val Leu Thr Ile Ala Leu Pro Val Pro
                35                  40                  45

Val Ile Val Ser Asn Phe Ala Met Tyr Tyr Ser His Thr Gln Ala Arg
        50                  55                  60

Ala Lys Leu
65

<210> SEQ ID NO 7
<211> LENGTH: 67
<212> TYPE: PRT
<213> ORGANISM: Unknown
<220> FEATURE:
<223> OTHER INFORMATION: Potassium Ion channel
<300> PUBLICATION INFORMATION:
<301> AUTHORS: Liu, Y., et al.
<302> TITLE: Neuron
<304> VOLUME: 19
<306> PAGES: 175-184
<307> DATE: 1997-07-01

<400> SEQUENCE: 7

Asn Ile Pro Ile Gly Phe Trp Trp Ala Val Val Thr Met Thr Thr Leu
 1               5                  10                  15

Gly Tyr Gly Asp Met Tyr Pro Gln Thr Trp Ser Gly Met Leu Val Gly
                20                  25                  30

Ala Leu Cys Ala Leu Ala Gly Val Leu Thr Ile Ala Met Pro Val Pro
                35                  40                  45
```

```
Val Ile Val Asn Asn Phe Gly Met Tyr Tyr Ser Leu Ala Met Ala Lys
    50                  55                  60

Gln Lys Leu
65

<210> SEQ ID NO 8
<211> LENGTH: 67
<212> TYPE: PRT
<213> ORGANISM: Unknown
<220> FEATURE:
<223> OTHER INFORMATION: Potassium Ion channel

<400> SEQUENCE: 8

Asn Ile Pro Ile Gly Phe Trp Trp Ala Val Val Thr Met Thr Thr Leu
  1               5                  10                  15

Gly Tyr Gly Asp Met Tyr Pro Lys Thr Trp Ser Gly Met Leu Val Gly
             20                  25                  30

Ala Leu Cys Ala Leu Ala Gly Val Leu Thr Ile Ala Met Pro Val Pro
         35                  40                  45

Val Ile Val Asn Asn Phe Gly Met Tyr Tyr Ser Leu Ala Met Ala Lys
    50                  55                  60

Gln Lys Leu
65

<210> SEQ ID NO 9
<211> LENGTH: 67
<212> TYPE: PRT
<213> ORGANISM: Unknown
<220> FEATURE:
<223> OTHER INFORMATION: Potassium Ion channel
<300> PUBLICATION INFORMATION:
<301> AUTHORS: Liu, Y., et al.
<303> JOURNAL: Neuron
<304> VOLUME: 19
<306> PAGES: 175-184
<307> DATE: 1997-07-01

<400> SEQUENCE: 9

Ser Ile Pro Ala Ala Phe Trp Tyr Thr Ile Val Thr Met Thr Thr Leu
  1               5                  10                  15

Gly Tyr Gly Asp Met Val Pro Glu Thr Ile Ala Gly Lys Ile Val Gly
             20                  25                  30

Gly Val Cys Ser Leu Ser Gly Val Leu Val Ile Ala Leu Pro Val Pro
         35                  40                  45

Val Ile Val Ser Asn Phe Ser Arg Ile Tyr His Gln Asn Gln Arg Ala
    50                  55                  60

Asp Lys Arg
65

<210> SEQ ID NO 10
<211> LENGTH: 67
<212> TYPE: PRT
<213> ORGANISM: Unknown
<220> FEATURE:
<223> OTHER INFORMATION: Potassium Ion channel
<300> PUBLICATION INFORMATION:
<301> AUTHORS: Liu, Y., et al.
<303> JOURNAL: Neuron
<304> VOLUME: 19
<306> PAGES: 175-184
<307> DATE: 1997-07-01

<400> SEQUENCE: 10
```

```
Ser Ile Pro Ala Ala Phe Trp Tyr Thr Ile Val Thr Met Thr Thr Leu
1               5                   10                  15

Gly Tyr Gly Asp Met Val Pro Ser Thr Ile Ala Gly Lys Ile Phe Gly
            20                  25                  30

Ser Ile Cys Ser Leu Ser Gly Val Leu Val Ile Ala Leu Pro Val Pro
            35                  40                  45

Val Ile Val Ser Asn Phe Ser Arg Ile Tyr His Gln Asn Gln Arg Ala
        50                  55                  60

Asp Lys Arg
65

<210> SEQ ID NO 11
<211> LENGTH: 67
<212> TYPE: PRT
<213> ORGANISM: Unknown
<220> FEATURE:
<223> OTHER INFORMATION: Potassium Ion channel
<300> PUBLICATION INFORMATION:
<301> AUTHORS: Liu, Y., et al.
<303> JOURNAL: Neuron
<304> VOLUME: 19
<306> PAGES: 175-184
<307> DATE: 1997-07-01

<400> SEQUENCE: 11

Ser Ile Pro Ala Ala Phe Trp Tyr Thr Ile Val Thr Met Thr Thr Leu
1               5                   10                  15

Gly Tyr Gly Asp Met Val Pro Lys Thr Ile Ala Gly Lys Ile Phe Gly
            20                  25                  30

Ser Ile Cys Ser Leu Ser Gly Val Leu Val Ile Ala Leu Pro Val Pro
            35                  40                  45

Val Ile Val Ser Asn Phe Ser Arg Ile Tyr His Gln Asn Gln Arg Ala
        50                  55                  60

Asp Lys Arg
65
```